US005766125A

United States Patent [19]

Aoyagi et al.

[11] Patent Number: 5,766,125
[45] Date of Patent: Jun. 16, 1998

[54] APPARATUS FOR DETERMINING THE CONCENTRATION OF LIGHT-ABSORBING MATERIALS IN BLOOD

[75] Inventors: Takuo Aoyagi; Masayoshi Fuse; Michio Kanemoto; Cheng-tai Xie; Naoki Kobayashi; Hideaki Hirahara, all of Tokyo, Japan

[73] Assignee: Nihon Kohden Corporation, Tokyo, Japan

[21] Appl. No.: 429,545

[22] Filed: Apr. 27, 1995

[30] Foreign Application Priority Data

Apr. 28, 1994 [JP] Japan .................................. 6-092616
Jan. 17, 1995 [JP] Japan .................................. 7-004820

[51] Int. Cl.$^6$ ............................................ A61B 5/000
[52] U.S. Cl. ..................................... 600/310; 600/322
[58] Field of Search ........................... 128/633, 664–7; 356/39–41; 600/310, 322, 314–316, 323, 326, 328

[56] References Cited

U.S. PATENT DOCUMENTS

| | | |
|---|---|---|
| 4,714,341 | 12/1987 | Hamaguri et al. |
| 5,028,787 | 7/1991 | Rosenthal et al. ................. 128/633 |
| 5,127,406 | 7/1992 | Yamaguchi ........................ 128/633 |
| 5,560,355 | 10/1996 | Merchant et al. .................. 128/633 |

FOREIGN PATENT DOCUMENTS

| | | | |
|---|---|---|---|
| A20194105 | 9/1986 | European Pat. Off. ....... G01N 21/31 |
| 0276477 | 3/1988 | European Pat. Off. ......... A61B 5/02 |
| A10276477 | 8/1988 | European Pat. Off. ......... A61B 5/02 |
| 8801147 | 2/1988 | WIPO ............................. A61B 5/00 |
| 8801148 | 2/1988 | WIPO ............................ A61B 21/31 |

OTHER PUBLICATIONS

"Theoretical and Experimental Study of Optical Attenuation of Blood," Takuo Aoyagi, revised Oct. 14, 1991, R&D Center, Nihon Kohden Corporation.

*Primary Examiner*—Jennifer Bahr
*Assistant Examiner*—Bryan K. Yarnell
*Attorney, Agent, or Firm*—Sughrue, Mion, Zinn, Macpeak & Seas, PLLC

[57] ABSTRACT

Light beams of different wavelengths, emitted from a light generating device, are transmitted through a living tissue. The transmitted light beams are converted into electrical signals by a photoelectric transducing device. A pulsation calculating device calculates a pulsation of an absorbance of tissue of a living tissue for each wavelength on the basis of the output signal of the photoelectric transducing device. By using this, a pulsation ratio calculating device calculates the ratio of the pulsations of the absorbance values. A concentration calculating device puts the output signal of the pulsation ratio calculating device into a formula having a single unknown on the tissue term, which is constructed on the basis of the fact that a predetermined relation is present between the tissue terms of the respective wavelengths, thereby calculating a value of the tissue term and the concentration of light absorbing material in blood.

13 Claims, 12 Drawing Sheets

APPARATUS FOR DETERMINING THE CONCENTRATION OF LIGHT-ABSORBING MATERIALS IN BLOOD

BACKGROUND OF THE INVENTION

1. Field of the Invention

The present invention relates to an apparatus for determining the concentration of light-absorbing materials in blood, such as oxygen saturation, abnormal hemoglobin concentration, injected dye concentration, and other light-absorbing materials.

2. Related Art

There is known an apparatus for determining a hemoglobin oxygen saturation and dye concentration in blood. In the apparatus, light beams of different wavelengths are projected into a living body, respective intensities Ii (i=1, 2, ... ) of the light beams transmitted through the living body are converted into corresponding electrical signals, pulsations $\Delta \ln Ii$ (i=1, 2, ... ) of absorbance in the tissue at the wavelengths are obtained, and a hemoglobin oxygen saturation and dye concentration in blood are determined on the basis of the pulsations.

In measuring an oxygen saturation S, the following equations can be constructed on the basis of Arthur Schuster's theory and its experiments.

$$\Phi_{32}=\Delta \ln I_3/\Delta \ln I_2=(Eb_3-Ex_3)/(Eb_2-Ex_2) \quad (1)$$

$$Eb_i=\{Eh_i(Eh_i+F)\}^{1/2} (i=2, 3) \quad (2)$$

$$Eh_i=SE_{oi}+(1-S)Er_i (i=2, 3) \quad (3)$$

where

Ebi: term caused by a pulsation of blood on wavelength $\lambda i$ (i=2, 3). Ebi will be referred to as a blood term.

Exi: term caused by a pulsation of tissues other than blood on wavelength $\lambda i$ (i=2, 3). Exi will be referred to as a tissue term.

Ehi: extinction coefficient of hemiglobin on wavelength $\lambda i$ (i=2, 3).

F: scattering coefficient.

S: oxygen saturation.

Eo: extinction coefficient

Er: extinction coefficient reduced hemoglobin

Examples of the wavelengths are: $\lambda 2=890$ nm, and $\lambda 3=665$ nm.

In the equations (2) and (3), F, Eo and Er are known. Then, in the right side of the equation (1), Eb2 and Eb3 are expressed as functions in which the only variable is S. In the right side of the equation (1), S, Ex2 and Ex3 are unknown. In the conventional art, $\Phi_{32}$ is converted into S on the basis of the empirically obtained relation between $\Phi_{32}$ and S (oxygen saturation), because the above-mentioned theory was not known.

In measuring the concentration of dye in blood when it is injected into a living tissue, the following equations can also be constructed on the basis of Arthur Schuster's theory and its experiments.

$$\Phi_{12}=\Delta \ln I_1/\Delta \ln I_2=(Eb_1-Ex_1)/(Eb_2-Ex_2) \quad (4)$$

$$Eb_i=\{(Eh_i+Ed_i\ Cd/Hb)(Eh_i+Ed_i\ Cd/Hb+F)\}^{1/2}(i=1, 2) \quad (5)$$

$$Eh_i=SE_{oi}+(1-S)Er_i \quad (6)$$

where

Ebi: blood term on wavelength $\lambda i$

Exi: tissue term on wavelength $\lambda i$

Ehi: extinction coefficient of hemoglobin on wavelength $\lambda i$

Edi: extinction coefficient of dye on wavelength $\lambda i$

Cd: concentration of dye in blood

Hb: concentration of hemoglobin in blood

Examples of the wavelengths are: $\lambda 1=805$ nm, and $\lambda 2=890$ nm.

In the equations (5) and (6), F, Eo, Er, Edi and Ed2 are known. Then, the unknowns in the right side of the equation (4) are S, Hb, Cd, Exi and Ex2. As long as the above wavelengths are used, the oxygen saturation S may be considered as S=1. If the hemoglobin concentration Hb is obtained by another measurement, the unknowns are Cd, Exi and Ex2. In the conventional art, it is presumed that Ex1 and Ex2 are approximately 0. By using the equation based on this presumption, the dye concentration Cd was calculated from $\Phi 2$.

The conventional measuring apparatus as mentioned above is unsatisfactory in its consideration of the influence by the tissue. A measurement error is inevitably caused and thus the measurement accuracy is not high.

SUMMARY OF THE INVENTION

An object of the present invention is to provide an apparatus which takes into consideration the influence by the tissue, and can determine oxygen saturation, dye concentration, and the concentration of light-absorbing materials in blood by using pulsative transmitted light.

According to an embodiment of the present invention, there is provided an apparatus for determining the concentration of light absorbing materials in blood, which comprises: light generating means for generating light beams of different wavelengths; photoelectric transducing means for converting light beams, which are emitted from the light generating means, and transmitted through a living tissue, into electrical signals; pulsation calculating means for calculating a pulsation of an absorbance of a living tissue for each wavelength on the basis of the output signal of the photoelectric transducing means; pulsation ratio calculating means for calculating the ratio of the pulsations of the absorbance values, calculated by the pulsation calculating means; and concentration calculating means for performing the calculations of a value of a tissue term and the concentration of light absorbing materials in blood on the basis of the output signal of the pulsation ratio calculating means, the concentration calculating means calculating a formula having a single unknown on the tissue term, which is constructed on the basis of the fact that a predetermined relation is present between the tissue terms of the respective wavelengths.

According to the present invention, the predetermined relation, which is present between the tissue terms of the respective wavelengths, is such a relation that each tissue term of respective wavelength are expressed by a linear function of a single tissue term.

Another embodiment of the present invention includes an apparatus for determining the concentration of light absorbing materials in blood comprising light generating means for generating light beams of different wavelengths; photoelectric transducing means for converting light beams, which are emitted from the light generating means, and transmitted through a living tissue, into electrical signals; pulsation calculating means for calculating a pulsation of an absorbance of tissue of a living tissue for each wavelength on the basis of the output signal of the photoelectric transducing means; pulsation ratio calculating means for calculating the ratio of the pulsations of the absorbance values, calculated by the pulsation calculating means; indication signal generating means for generating a signal indicative of the fact that dye is injected into blood; first concentration calculating means for performing the calculations of a value of a tissue term or the value of a tissue term and the concentration of light absorbing materials in blood on the basis of the output signal of the pulsation ratio calculating means, the first concentration calculating means calculating a formula having a single unknown on the tissue term, which is constructed on the basis of the fact that a predetermined relation is present between the tissue terms of the respective wavelengths; and second concentration calculating means for performing the calculations of the concentration of dye in blood or the concentration of dye in blood and the concentration of light absorbing materials in blood on the basis of the output signal of the pulsation ratio calculating means after the indicating signal generating means generates an indication signal, and the value of a tissue term obtained by the first concentration calculating means before the indication signal is generated.

According to the present invention, the concentration value of injected dye in the first concentration calculating means is set to zero.

According to the present invention, light beams of different wavelengths, emitted from a light generating means, are transmitted through a living tissue. The transmitted light beams are converted into electrical signals by a photoelectric transducing means. A pulsation calculating means calculates a pulsation of an absorbance of tissue of a living tissue for each wavelength on the basis of the output signal of the photoelectric transducing means. By using this, a pulsation ratio calculating means calculates the ratio of the pulsations of the absorbance values. A concentration calculating means uses the output signal of the pulsation ratio calculating means in a formula having a single unknown on the tissue term, which is constructed on the basis of the fact that a predetermined relation is present between the tissue terms of the respective wavelengths, thereby calculating a value of the tissue term and the concentration of light absorbing material in blood.

According to the present invention, the concentration calculating means calculates such a relation that tissue terms of wavelengths are expressed by a linear function of a single tissue term.

According to the present invention, light beams of different wavelengths, emitted from a light generating means, are transmitted through a living tissue. The transmitted light beams are converted into electrical signals by a photoelectric transducing means. A pulsation calculating means calculates a pulsation of an absorbance of tissue of a living tissue for each wavelength on the basis of the output signal of the photoelectric transducing means. A pulsation ratio calculating means calculates the ratio of the pulsations of the absorbance values. The first concentration calculating means performs the calculations of a value of a tissue term or the value of a tissue term and the concentration of light absorbing materials in blood by using the output signal of the pulsation ratio calculating means, in a formula having a single unknown on the tissue term, which is constructed on the basis of the fact that a predetermined relation is present between the tissue terms of the respective wavelengths. When the indication signal generating means generates an indication signal, the second concentration calculating means calculates the concentration of dye in blood or the concentration of dye in blood and the concentration of light absorbing materials in blood by using the output signal of the pulsation ratio calculating means, and the value of a tissue term obtained by the first concentration calculating means before the indication signal is generated.

According to the present invention, the concentration calculating means calculates such a relation that tissue terms of wavelengths are expressed by a linear relation of a single tissue term.

According to the present invention, the same formula is used by the first and second concentration calculating means, and when the formula is used by the first concentration calculating means, the concentration of injected dye is zero.

DETAILED DESCRIPTION OF THE PREFERRED EMBODIMENTS

Figure 1:
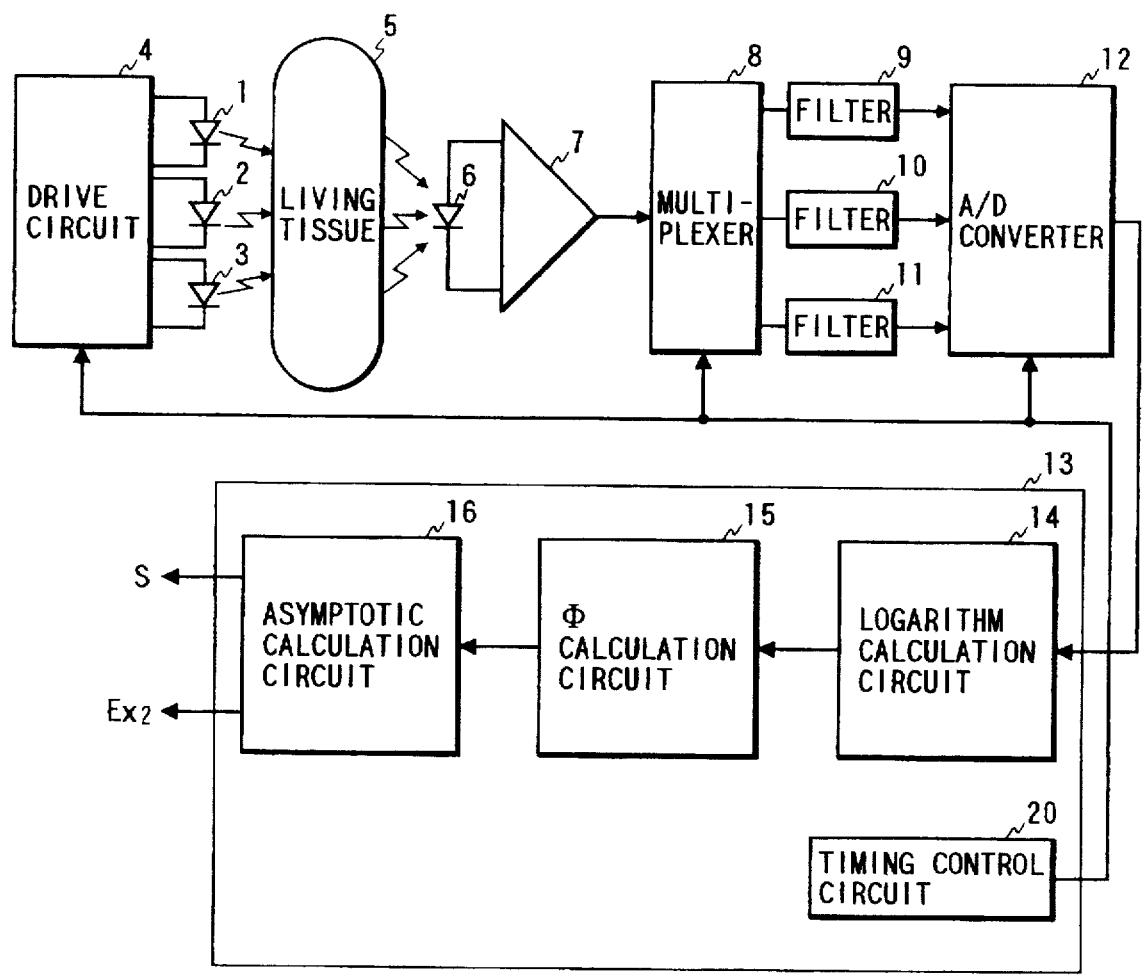
FIG. 1 is a block diagram showing an overall arrangement of the first embodiment.

The principles of an apparatus for determining oxygen saturation in blood, which is a first embodiment of the present invention, will be described below.

First Embodiment

Light beams of wavelengths $\lambda 1$, $\lambda 2$ and $\lambda 3$ are projected into a living tissue. The light beams I1, I2 and I3 that are transmitted through the living tissue are transformed into corresponding electrical signals. The logarithms of the electrical signals are taken to obtain the pulsative components $\Delta \ln I1$, $\Delta \ln I2$ and $\Delta \ln I3$ of the electrical signals. In these denotations of the pulsative components, suffixes 1, 2 and 3 indicate the wavelengths $\lambda_1$, $\lambda_2$ and $\lambda_3$ respectively.

In a case where the light-absorbing material contained in blood is only hemoglobin, it can be approximated by oxyhemoglobin $O_2Hb$ and deoxyhemoglobin $RHb$, the following equations hold. The reason why the equations hold have clearly been described by our theory and experiments based on Arthur Schuster's theory and its experiments.

$$\Phi_{12}=\Delta \ln I1/\Delta \ln I2=(Eb1-Ex1)/(Eb2-Ex2) \quad (11)$$

$$\Phi_{32}=\Delta \ln I3/\Delta \ln I2=(Eb3-Ex3)/(Eb2-Ex2) \quad (12)$$

where

Ebi (i=2, 3): blood term
Exi (i=2, 3): tissue term $$Ebi=\{Ehi(Ehi+F)\}^{1/2} (i=1, 2, 3) \quad (13)$$

$$Ehi=SEoi+(1-S)Eri (i=1, 2, 3) \quad (14)$$

Eh: extinction coefficient of hemiglobin
F: scattering coefficient
S: oxygen saturation
Eo: extinction coefficient of oxyhemoglobin (known)
Er: extinction coefficient of reduced hemoglobin (known)
An object to be measured is oxygen saturation.

In the equations (11) and (12), Ebi (i=1, 2, 3) is the function containing only S as a variable as seen from the equations (13) and (14). Then, the unknowns are S and Exi (i=1, 2 and 3).

The tissue term Exi (I=1, 2, and 3) can theoretically be written by $$Exi=(Zxi/Hb)(\Delta Dt/\Delta Db) \quad (15)$$

Exi indicates an extinction coefficient of a pure tissue (tissue other than blood), which has a wavelength dependency mainly for light absorption by water. Within the wavelengths handled here, this extinction coefficient may be considered as substantially constant.

Hb indicates a hemoglobin concentration, which varies depending on individuals.

$\Delta Dt/\Delta Db$ is the ratio of a pulsation $\Delta Dt$ of the thickness of the pure tissue and a pulsation $\Delta Db$ of the thickness of blood. The ratio varies depending on individuals and a mounting state of the probe.

Accordingly, the tissue term can be approximated as Ex1=Ex2=Ex3.

Actually, the approximation of the tissue term is slightly different from the above one because of the structure of the probe and the optical characteristics of the tissue of the living tissue. Generally, the following equations hold among Ex1, Ex2 and Ex3.

$$Ex1=a1Ex2+b1 \quad (16)$$

$$Ex3=a3Ex2+b3 \quad (17)$$

where a1, a3, b1 and b3 are known constants. These values vary depending on the structures of the probes used, and can be obtained in advance for the probes used.

Figure 9:
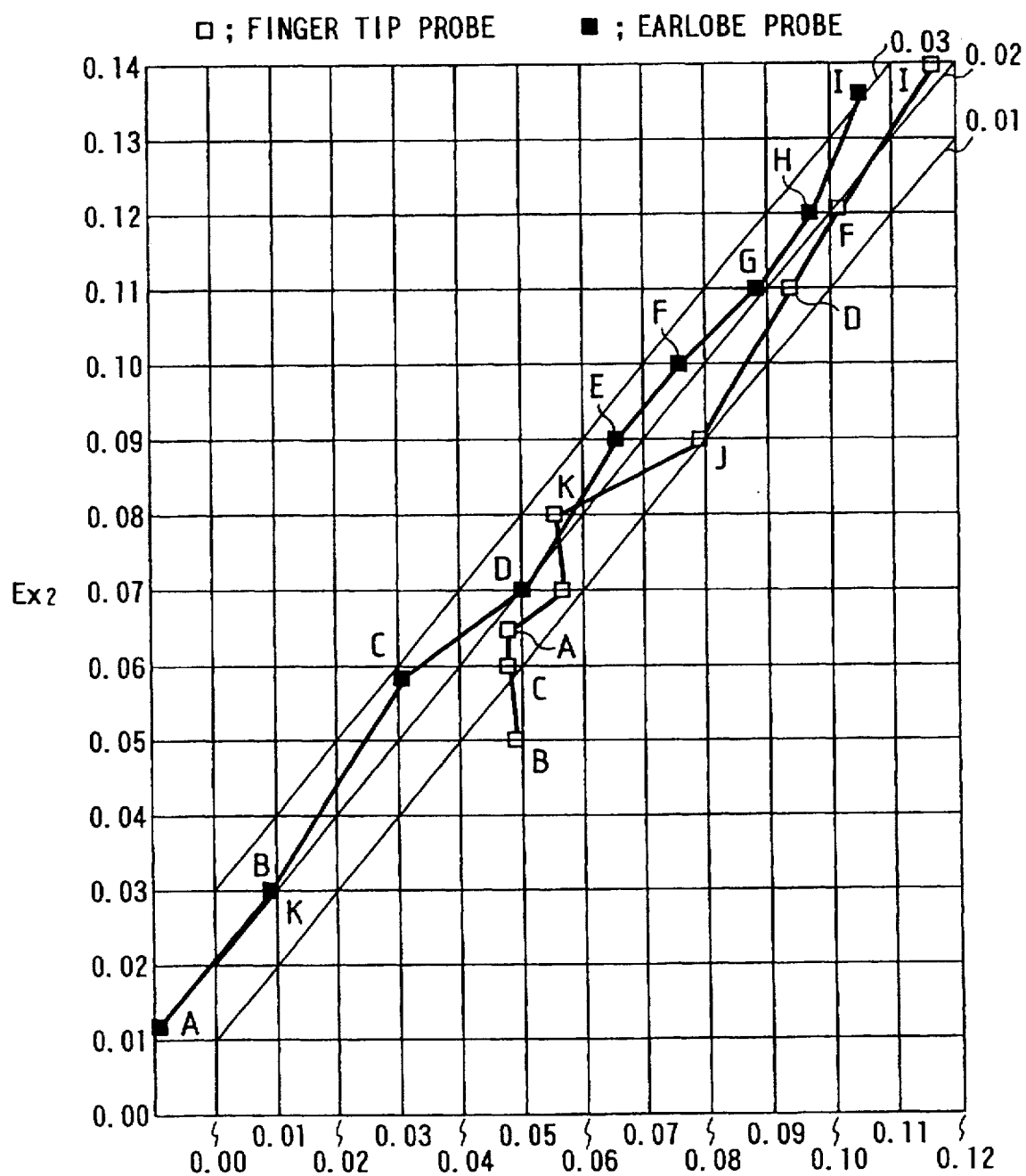
FIG. 9 is a graph showing actually measured values of the tissue terms Ex1 and Ex2 of two wavelengths.

Thus, the tissue term of a wavelength is described by a linear expression containing the tissue term of another wavelength. This fact was empirically confirmed. Ex1 and Ex2 of a plural number of subjects were measured using light of two different wavelengths λ1 and λ2. The results of the measurement are shown in FIG. 9. In the figure, A, B, C, ... indicate the names of the subjects; white square marks, the measured values when a finger tip probe is used; black square marks, the measured values when an ear lobe is used.

A method of the measurement of the data will be described. Light beams of wavelengths λ1 and λ2 are projected into a living tissue. The light beams I1 and I2 that are transmitted through the living tissue are transformed into corresponding electrical signals. The logarithms of the electrical signals are taken to obtain the pulsative components $\Delta \ln I1$, $\Delta \ln I2$ and $\Delta \ln I3$. When the light-absorbing materials in blood are only injected dye and hemoglobin, the following equation holds:

$$\Phi_{12} = \Delta \ln I_1/\Delta \ln I_2 = \quad (18)$$

$$[\{(Eh_1 + Ed_1Cd/Hb)(Eh_1 + Ed_1Cd/Hb + F)\}^{1/2} - Ex_1]/$$

$$[\{(Eh_2 + Ed_2Cd/Hb)(Eh_2 + Ed_2Cd/Hb + F)\}^{1/2} - Ex_2]$$

where Eh1 and Eh2 are extinction coefficients of hemoglobin, Hb is the concentration of hemoglobin in blood, Cd is the concentration of dye in blood, and Ed1 and Ed2 are extinction coefficients of injected dye.

$\Phi_{120}$ as $\Phi_{12}$ when the concentration of dye in blood is zero (0) is given by the following equation (19).

$$\Phi_{120}=[\{Eh_1(Eh_1+F)\}^{1/2}-Ex_1]/[\{Eh_2(Eh_2+F)\}^{1/2}-Ex_2] \quad (19)$$

In the above equations, Eh1 and Eh2 are known. $\Phi_{12}$ and $\Phi_{120}$ were measured, and Cd/Hb was measured with sampled blood. The results are put into the equations (18) and (19). These equations were simultaneously solved, thereby obtaining Ex1 and Ex2. Data plotted in FIG. 9 indicate the results of the measurement conducted for a plural number of subjects. In the example of FIG. 9, a1=1, b1=−0.025 [dL/gcm] for the finger tip probe, and a1=1, b1=−0.015 [dL/gcm] for the ear lobe probe.

In this instance, two different wavelengths are used for the measurement. If three or more wavelengths are used, the relation between Ex1 and Ex2 and the relation between Ex3 and Ex2 etc are similarly obtained. Thus calculation of the constants A and B is effected by solving the equations. Next the determination of the concentration of light absorbing materials in the blood.

Since the relation as mentioned above are present among Ex1, Ex2 and Ex3, the unknowns in the equations (11) and (12) are S and Ex2. The equations (11) and (12) can be rewritten into $$Ex2=f1(S, \Phi_{12}) \quad (20)$$

$$S=f2(Ex2, \Phi_{32}) \quad (21)$$

This simultaneous equations is a nonlinear simultaneous equations, and hence cannot be solved algebraically. Then, the asymptotic calculation is used.

Figure 2:
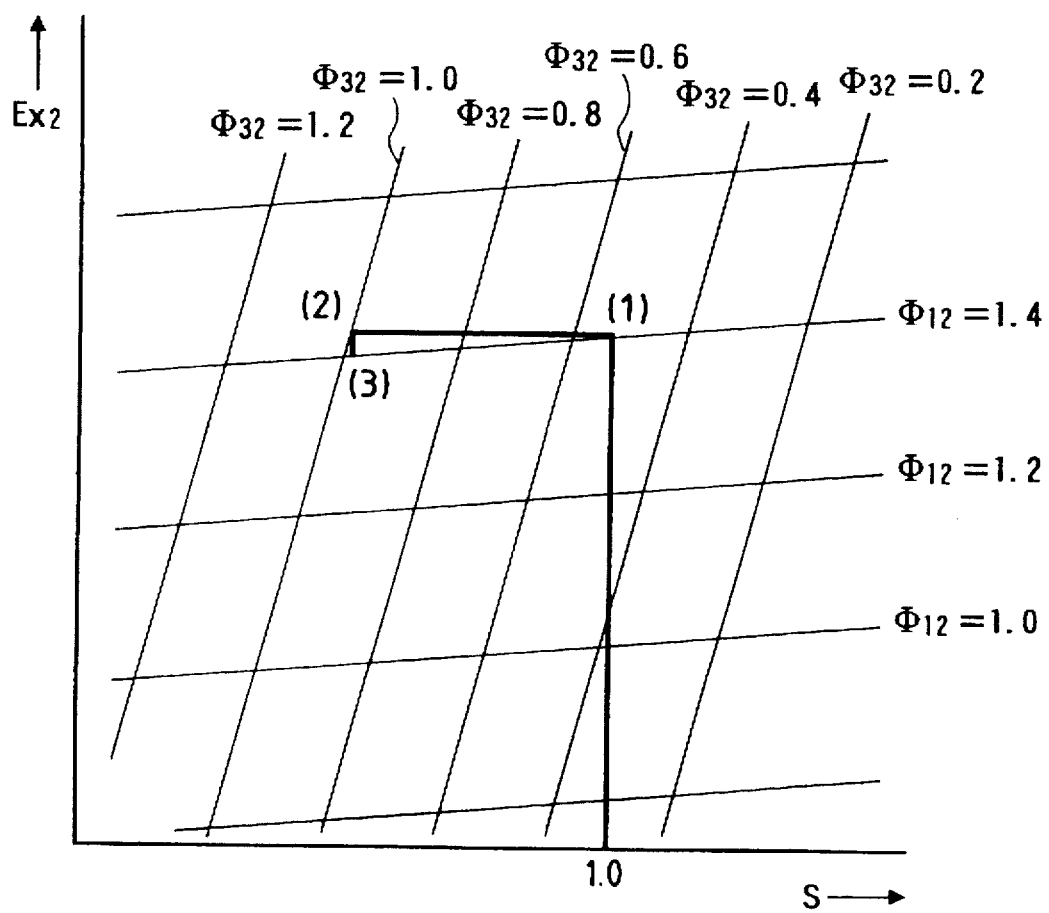
FIG. 2 is a graph useful in explaining the operation of the first embodiment.

$\Phi_{12}$ and $\Phi_{32}$ are obtained in a manner that light is projected into a living tissue and calculation is made for $\Delta \ln I1/\Delta \ln I2$ and $\Delta \ln I3/\Delta \ln I2$. Ex2 is obtained by putting a proper value as a first approximate value to S in the equation (20). S is obtained by putting this Ex2 into the equation (21). Then, this S is put again into the equation (20), to thereby obtain Ex2. Repeating the calculation process, then S and Ex2 as limit values are obtained. FIG. 2 shows a process till S and Ex2 are obtained. In this instance, $\Phi_{12}$=1.4 and $\Phi_{32}$=1.0, and the initial value of S is 1.

Following the principle description, an apparatus arranged on the basis of the principle will be described. FIG. 1 illustrates in block diagram an overall arrangement of an apparatus for determining oxygen saturation in blood according to an embodiment of the present invention.

Light emitting elements 1, 2 and 3, when driven by a drive circuit 4, emit light beams of the wavelengths λ1, λ2 and λ3. These light beams are transmitted through a living tissue 5, and the light beams emanating from the tissue are received and converted into corresponding electrical signals by a photo sensing element 6. These signals are amplified by an amplifier 7, and then a multiplexer 8 directs these amplified signals to the filters 9, 10 and 11 in accordance with the wavelengths of the light beams. The filters 9 to 11 filter out unnecessary high frequency components of the electrical signals, an A/D converter 12 converts the electrical signals from the filters into digital signals, and the digital signals are inputted to a data processor 13. The data processor 13 is made up of a logarithm calculation circuit 14, a $\Phi$ calculation circuit 15, an asymptotic calculation circuit 16, and a timing control circuit 20. The timing control circuit 20 sends timing signals to the drive circuit 4, multiplexer 8, A/D converter 12, and the data processor 13, thereby time controlling the operations of these functional components.

The logarithm calculation circuit 14 logarithmically calculates the output signals I1, I2 and I3 of the A/D converter 12 into logarithmic signals lnI1, lnI2 and lnI3.

The $\Phi$ calculation circuit 15 extracts pulsative components from the logarithmic signals lnI1, lnI2 and lnI3 outputted from the logarithm calculation circuit 14, and calculates $\Phi_{12} = \Delta \ln I1/\Delta \ln I2$ and $\Phi_{32} = \Delta \ln I3/\Delta \ln I2$.

The asymptotic calculation circuit 16 puts $\Phi_{12}$ and $\Phi_{32}$, calculated by the $\Phi$ calculation circuit 15, into the equations (20) and (21), and performs the asymptotic calculation using those equations. In the calculation, the first S is set to 1, and the calculation is repeated a preset number of times. As the result of calculation, S and Ex2 are obtained. S is an oxygen saturation. This value is highly accurate since it is obtained in consideration with the influences by the tissue of the respective wavelengths.

Second Embodiment

Figure 3:
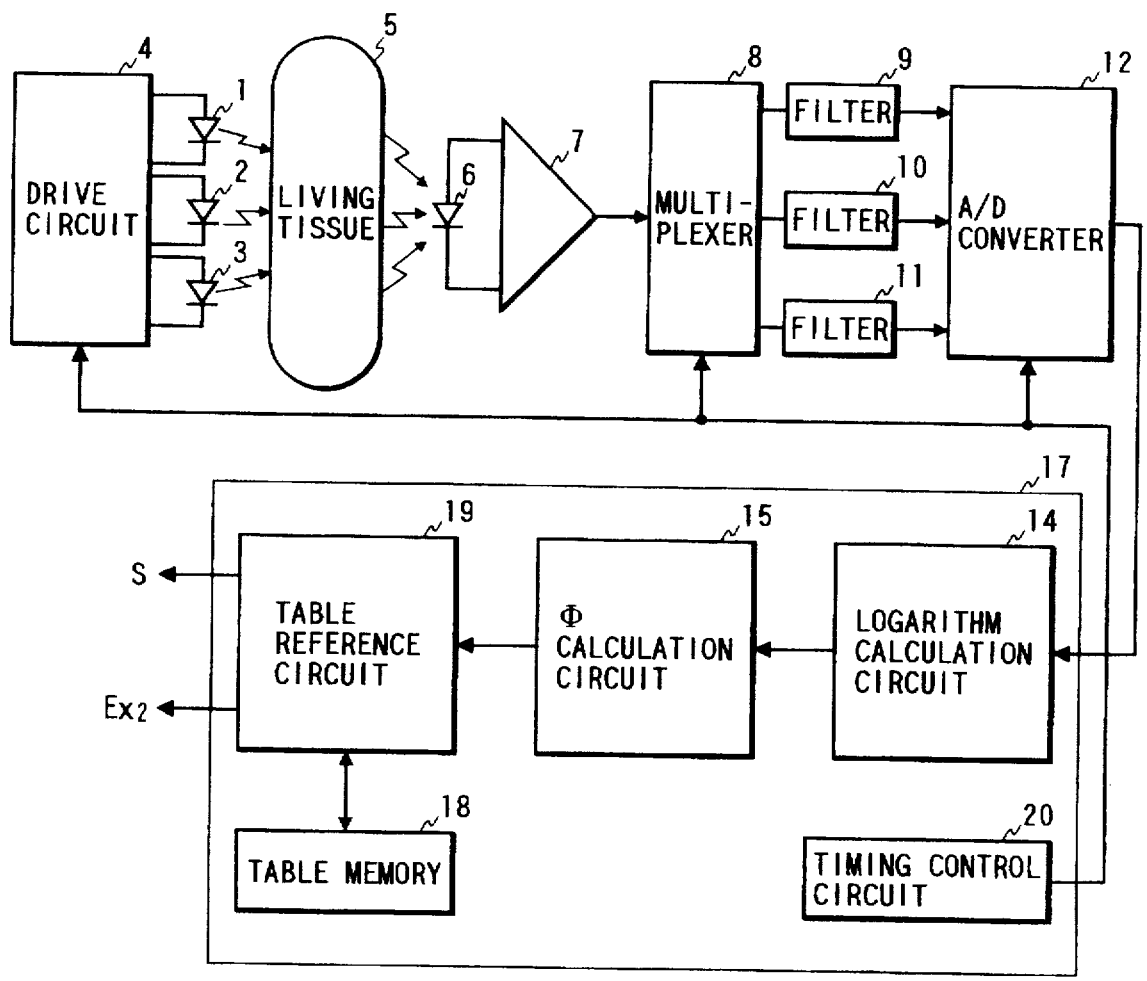
FIG. 3 is a block diagram showing an overall arrangement of the second embodiment.
Figure 4:
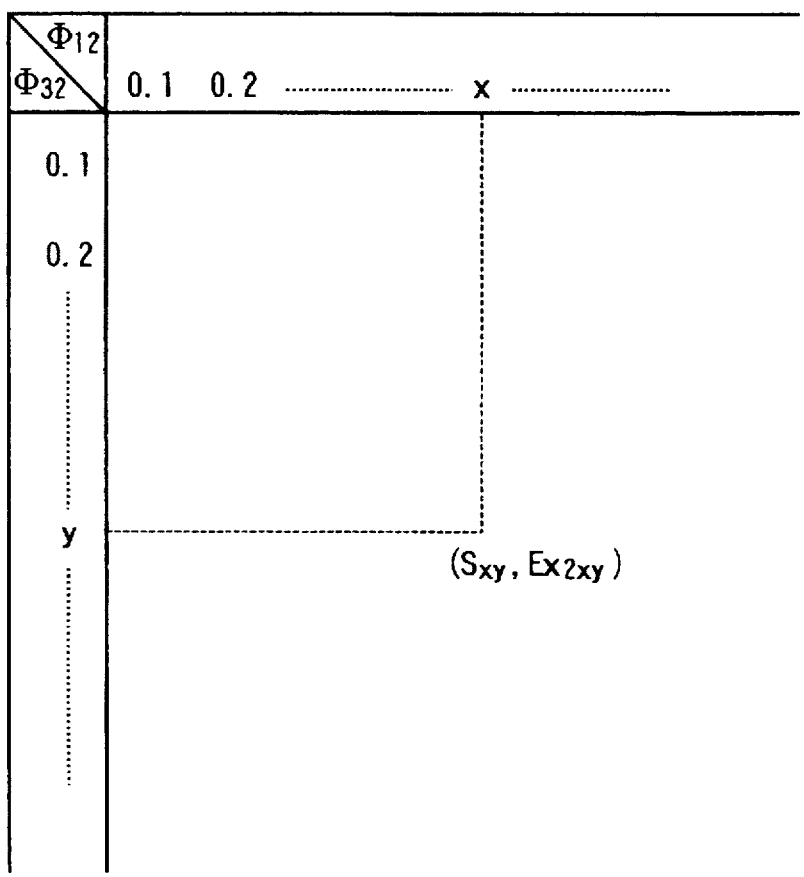
FIG. 4 is a diagram showing the contents of a table memory 18 shown in FIG. 3.

Another apparatus for determining oxygen saturation in blood according to a second embodiment of the present invention will be described. FIG. 3 shows in block form an overall arrangement of this apparatus. Like reference numerals are used for designating like or equivalent portions in the FIG. 1 apparatus. In the second embodiment, a data processor 17 is different from the data processor 13 in the first embodiment in that a table memory 18 and a table reference circuit 19 are used in place of the asymptotic calculation circuit 16. The table memory 18 stores a table containing sets of S and Ex2, which are defined by $\Phi_{12}$ and $\Phi_{32}$, as shown in FIG. 4. The table reference circuit 19 refers to the contents of the table, reads the values of S and Ex2 defined by $\Phi_{12}$ and $\Phi_{32}$ derived from the $\Phi$ calculation circuit 15, and outputs the real values. The useful effects of the first embodiment can be obtained also by the second embodiment thus arranged.

Third Embodiment

A third embodiment of the present invention will be described. The third embodiment is a dye dilution curve measuring apparatus. The principles of the third embodiment will first be described.

$$\Phi_{12} = \Delta \ln I1/\Delta \ln I2 = (Eb1-Ex1)/(Eb2-Ex2) \quad (22)$$

$$\Phi_{32} = \Delta \ln I3/\Delta \ln I2 = (Eb3-Ex3)/(Eb2-Ex2) \quad (23)$$

where $$Ebi = \{(Ehi+EdiCd/Hb)(Ehi+EdiCd/Hb+F)\}^{1/2} (i=1, 2, \text{ and } 3) \quad (24)$$

$$Ehi = SEoi+(1-S)Eri (i=1, 2, 3) \quad (25)$$

Ebi, Exi, Ehi, Hb, F, S, Eo, and Er are the same as those described in the first embodiment. Hb is measured in advance. Edi is an extinction coefficient of dye. Cd is an unknown concentration of dye in blood.

In the equations (22) and (23), Ebi is the function with variables S and Cd, as seen from the equations (24) and (25).

Since $\Phi_{12}$ and $\Phi_{32}$ are obtained by the measurement, the unknowns in the equations (22) and (23) are S, Cd and Exi (i=1, 2, 3). A fixed mutual relationship is present among the terms Exi. Ex1 and Ex3 can be expressed by a linear equation of Ex2, as referred to in the description of the first embodiment. Therefore, the unknowns are three, S, Cd, and Ex2.

(A) Before dye injection

Before dye is injected into a blood vessel, in the above equation, Cd=0, and then the unknowns are S and Ex2. The equations (22) and (23) are equal to the equations (13) and (14), respectively. S and Ex2 can be obtained in exactly the same manner as in the first embodiment. Accordingly, Ex1, Ex2, and Ex3 can be obtained.

(B) After dye injection

The values Ex1, Ex2, and Ex3 before dye injection are substantially equal to those after dye injection. Therefore, these values are assumed to be constant. Accordingly, the unknowns in the equations (22) and (23) are S and Cd after dye injection. The equations (22) and (23) can be rewritten into $$Cd = f3(S, \Phi_{12}, \Phi_{32}, Ex2) \quad (27)$$

$$S = f4(Cd, \Phi_{12}, \Phi_{32}, Ex2) \quad (28)$$

Figure 5:
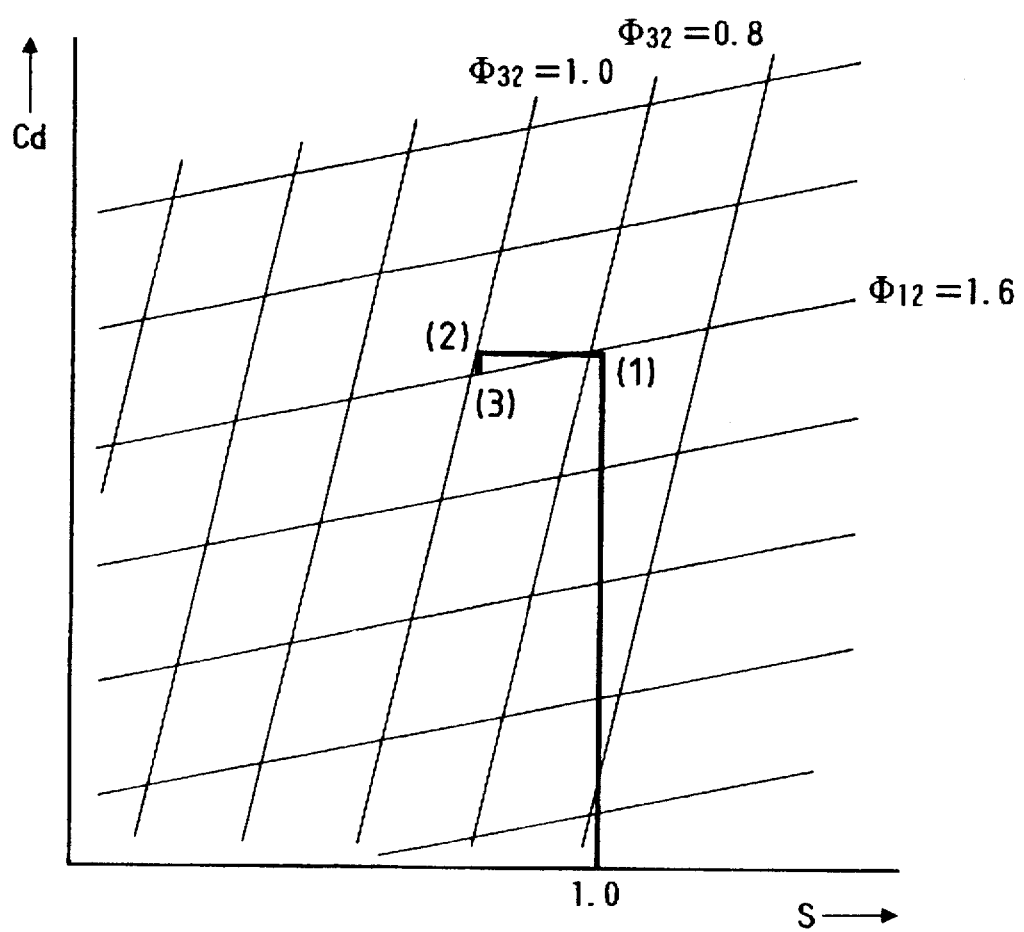
FIG. 5 is a graph useful in explaining the operation of a third embodiment of the invention.

This simultaneous system of equations can be solved using the asymptotic calculation. $\Phi_{12}$ and $\Phi_{32}$ can be obtained by the measurement. The method for obtaining Ex2 by the measurement before dye injection is as referred to the description of the oxygen saturation measurement. To obtain Cd, a proper value is substituted for S in the equation (27), to thereby obtain Cd. The resultant Cd is put used in the equation (28), to thereby obtain S. The obtained S is put used in the equation (27), thereby to obtain Cd. Repeating this calculation process, S and Cd as limit values are obtained. A process of iteration until S and Cd are obtained by this method is illustrated in FIG. 5. In this instance, $\Phi_{12}=1.6$ and $\Phi_{32}=1.0$, and the initial value of S is 1.

Figure 6:
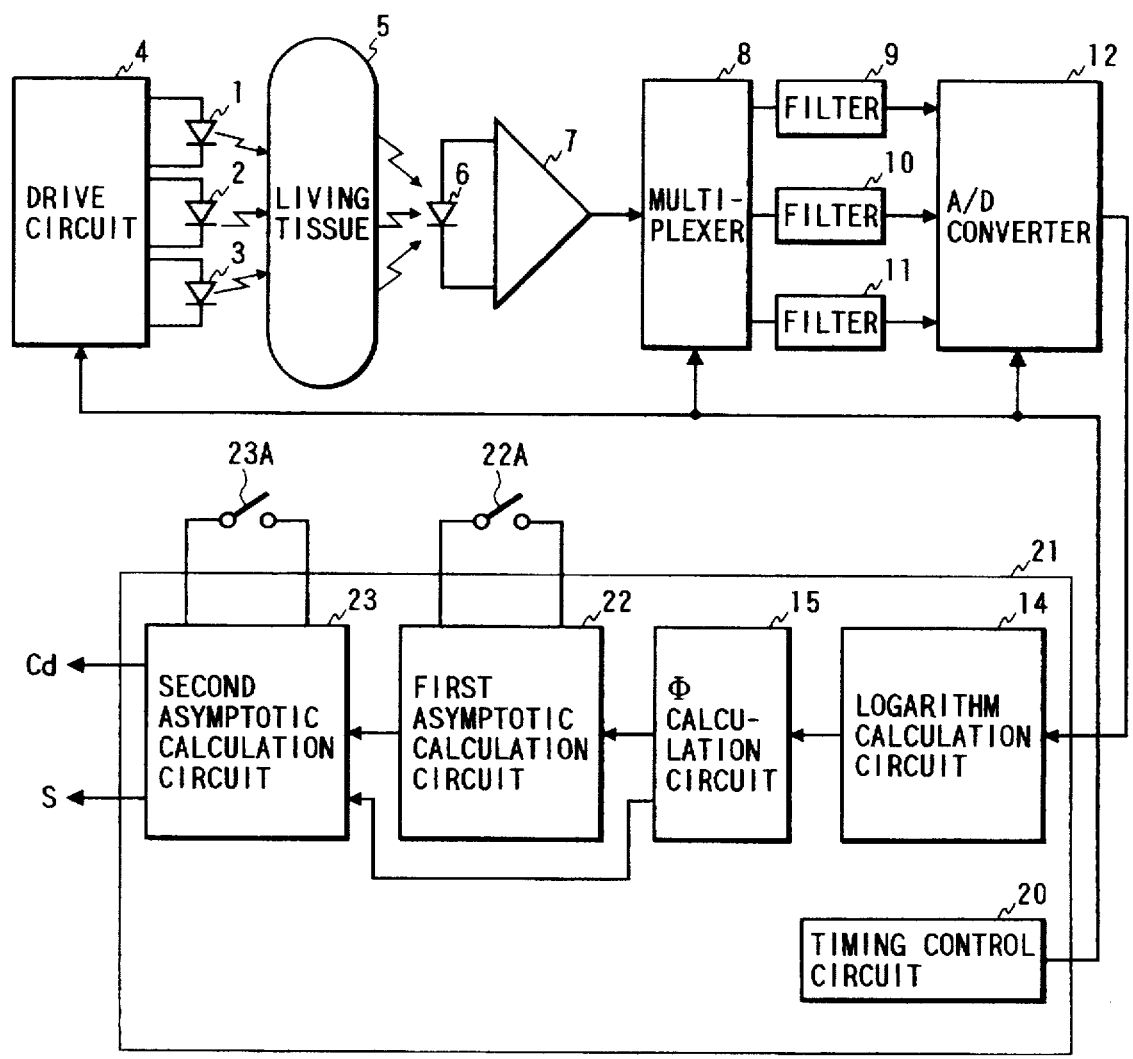
FIG. 6 is a block diagram showing an overall arrangement of the third embodiment.

The apparatus designed on the basis of the above-mentioned principles will be described. FIG. 6 illustrates in block form an overall arrangement of the apparatus. In the figure, like reference numerals are used for designating like or equivalent portions in FIG. 1 showing the first embodiment apparatus. A data processor 21 is made up of a logarithm calculation circuit 14, a $\Phi$ calculation circuit 15, a first asymptotic calculation circuit 22, a second asymptotic calculation circuit 23, and a timing control circuit 20. The operation of the data processor 21 will be described.

Before dye injection, Cd=0. When an operator turns on a switch 22A, the first asymptotic calculation circuit 22 puts $\Phi_{12}$ and $\Phi_{32}$, which are received from the $\Phi$ calculation circuit 15, into the equations (20) and (21), and carries out the asymptotic calculation using these equations. The calculation is the same as that in the first embodiment, and its description is omitted here. Thus, Ex2 is obtained.

Then, dye is injected into a living tissue, and a switch 23A is turned on. In turn, the second asymptotic calculation circuit 23 puts Ex2, which is received from the first asymptotic calculation circuit 22, and $\Phi_{12}$ and $\Phi_{32}$, which are received from the $\Phi$ calculation circuit 15, into the equations (27) and (28), and solves this simultaneous of equations using the asymptotic calculation. As the result of the calculation, S and Cd are obtained. When the second asymptotic calculation circuit 23 repeats this calculation process, a dye dilution curve is obtained.

Fourth Embodiment

Figure 7:
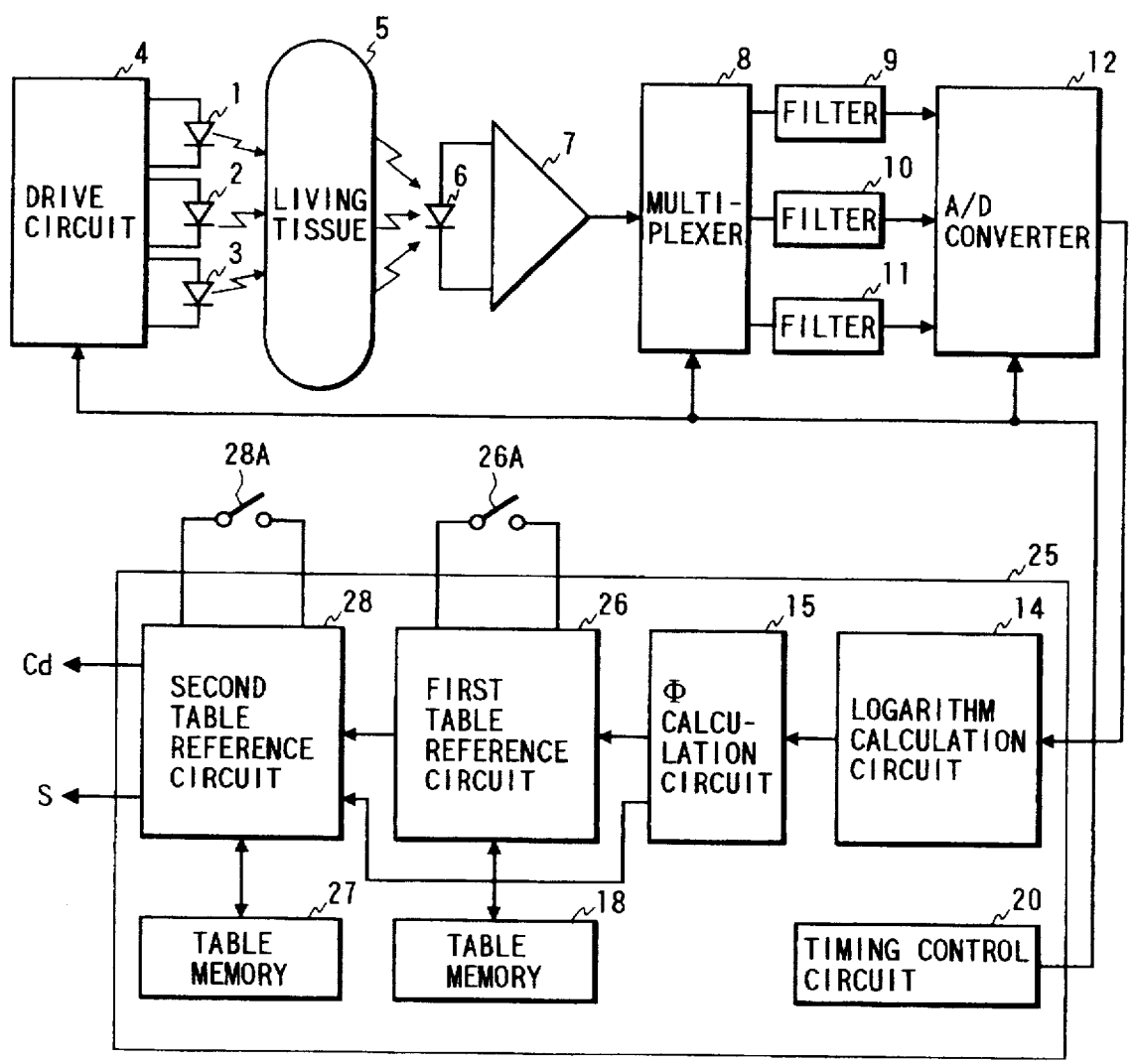
FIG. 7 is a block diagram showing an overall arrangement of a fourth embodiment of the present invention.
Figure 8:
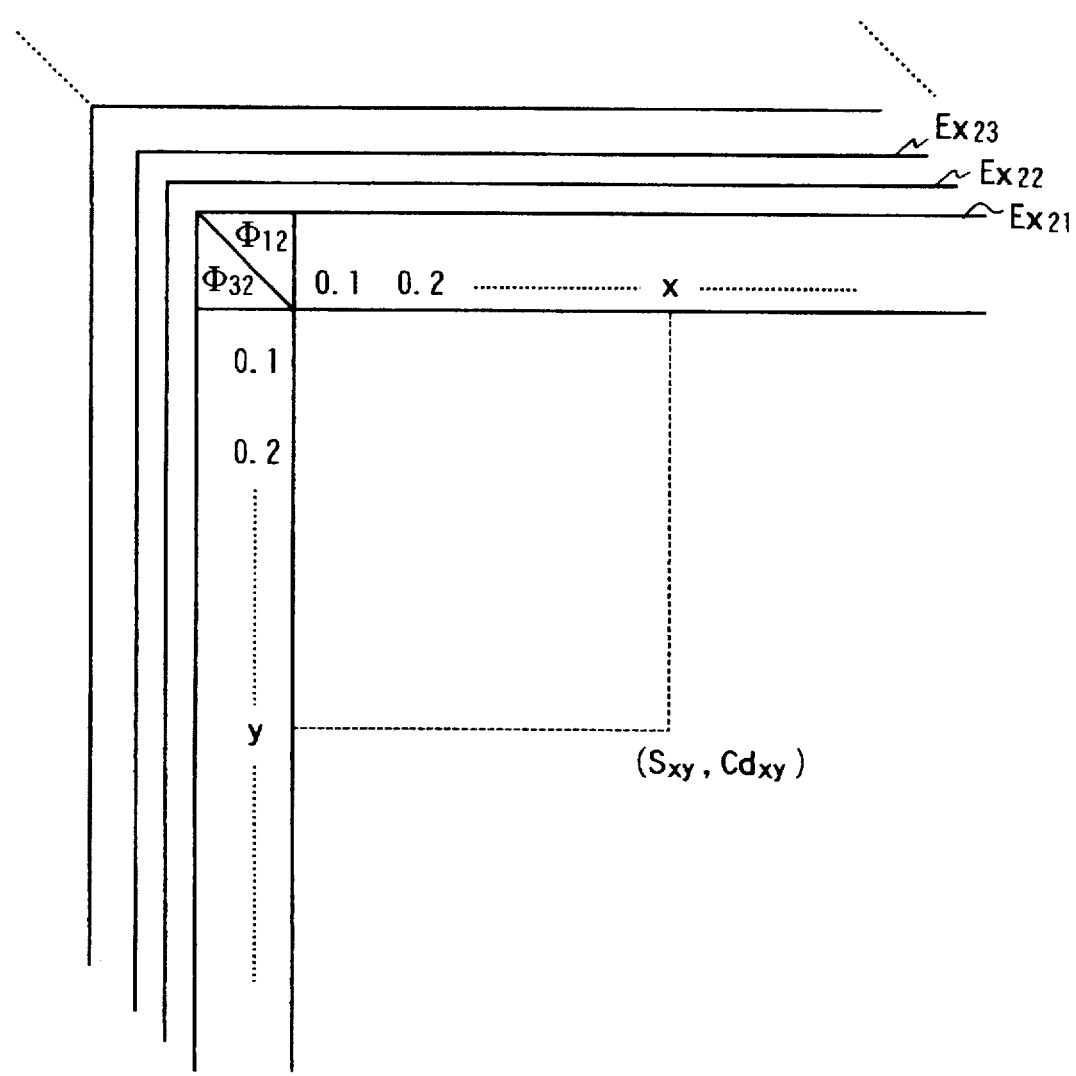
FIG. 8 is a diagram showing the contents of a table memory 29 shown in FIG. 7.

A fourth embodiment of the present invention will be described. The fourth embodiment is also a dye dilution curve measuring apparatus. FIG. 7 shows in block form an overall arrangement of the dye dilution curve measuring apparatus. As seen, the fourth embodiment apparatus is equivalent to the second embodiment apparatus which additionally uses a second table reference circuit 28 and a table memory 29. The second table reference circuit 28 is provided with a switch 28A, which is for indicating the injection of dye. A first table reference circuit 26, which corresponds to the table reference circuit 19, is provided with a switch 26A. The circuit starts to operate when this switch 26A is turned on by an operator. The contents of a table memory 27 are illustrated in FIG. 8. As illustrated, sets of Cd and S are defined by $\Phi_{12}$ and $\Phi_{32}$, which are provided for each of the terms Ex2. The operation of the data processor 25 will be described below.

Before dye is injected into a living tissue, the switch 26A is turned on, and the first table reference circuit 26 performs exactly the same process as the table reference circuit 19, and extracts S and Ex2, which correspond to $\Phi_{12}$ and $\Phi_{32}$ as the output signals of the $\Phi$ calculation circuit 15. Then, dye is injected, and the switch 28A is turned on. In turn, the second table reference circuit 28 selects a table on Ex2 extracted by the first table reference circuit 26, from among those tables in the table memory 27, and extracts a set of Cd and S defined by the $\Phi_{12}$ and $\Phi_{32}$ from the $\Phi$ calculation circuit 15. This apparatus requires a smaller amount of process steps, and hence quickly produces the measurement results. When the second table reference circuit 26 successively repeats this process, values of dye concentration Cd are successively obtained. As a result, a dye dilution curve measurement is carried out.

Fifth Embodiment

A fifth embodiment of the present invention will be described. The fifth embodiment is a dye dilution curve measuring apparatus. The principles on which the construction of the fifth embodiment are based will first be described. Light beams of wavelengths $\lambda 1$ (=805 nm) and $\lambda 2$ (=890 nm) are projected into a living tissue. The light beams I1 and I2 that are transmitted through the living tissue are transformed into corresponding electrical signals. The logarithms of the electrical signals are taken to obtain the pulsative components $\Delta \ln I1$ and $\Delta \ln I2$.

(A) Before dye injection

Before dye is injected into a living tissue, the following equation holds $$\Phi_{12} = \Delta \ln I1 / \Delta \ln I2 = (Eb1 - Ex1)/(Eb2 - Ex2) \qquad (29)$$

where Ebi: blood term caused by a pulsation in blood
Exi (i=1, 2): tissue term caused by a pulsation in blood $$Eb1 = \{Eh1(Eh1+F)\}^{1/2} \qquad (30)$$

$$Eb2 = \{Eh2(Eh2+F)\}^{1/2} \qquad (31)$$

Eh1 and Eh2 are extinction coefficients of hemoglobin. Eh1 and Eh2 at wavelengths $\lambda 1$ (=805 nm) and $\lambda 2$ (=890 nm) may be approximated to the extinction coefficients Eo1 and Eo2 of oxyhemoglobin. Hence, $$Eh1 = Eo1 \qquad (32)$$

$$Eh2 = Eo2 \qquad (33)$$

Since F is a scattering coefficient, $\Phi_{12}$ is the function of the unknowns Ex1 and Ex2.

It can be considered that the following relation holds between Ex1 and Ex2 as in the first embodiment $$Ex1 = a1 Ex2 + b1 \qquad (34)$$

a1 and b1 are fixed values that are previously measured. When substituting the equations (30), (31) and (34) into the equation (29), the we have $$\Phi_{12} = \Delta \ln I1 / \Delta \ln I2 = [\{Eh1(Eh1+F)\}^{1/2} - (a1Ex2+b1)]/[\{Eh2(Eh2+F)\}^{1/2} - Ex2] \qquad (35)$$

Therefore, if the actually measured value of $\Phi_{12}$ is given, Ex1 can be calculated.

If the measuring location is a location where the blood stream is stable, such as an ear lobe, Ex1 can be considered to be stable during the measurement.

(B) After dye injection

After dye injection, the following equation holds $$\Phi_{12} = \Delta \ln I1 / \Delta \ln I2 = [\{Eh1(Eh1+Ed1Cd/Hb)(Eh1+Ed1Cd/Hb+F)\}^{1/2} - Ex1]/[\{Eh2+Ed2Cd/Hb)(Eh2\ Ed2Cd/Hb+F)\}^{1/2} - Ex2] \qquad (36)$$

where Cd: dye concentration in blood
Ed1, Ed2: extinction coefficients of injected dye.

If dye is ICG (indocyanine-green), Ed2 can be considered to be zero. From this fact and the equation (34), the equation (36) can be rewritten into $$\Phi_{12} = \Delta \ln I1 / \Delta \ln I2 = [\{Eh1+Ed1Cd/Hb)(Eh1+Ed1Cd/Hb+F)\}^{1/2} - (a1Ex2+b1)]/[\{Eh2(Eh2+F)\}^{1/2} - Ex2] \qquad (37)$$

Eh1 and Eh2 may be approximated to Eo1 and Eo2, as described above. Eo1 and E02 are known, and Ed1 in the equation is also known. Ex2 is the value obtained before dye injection. Where the hemoglobin concentration Hb in blood is already measured, if $\Phi_{12}$ is obtained, the dye concentration Cd can be calculated.

Figure 10:
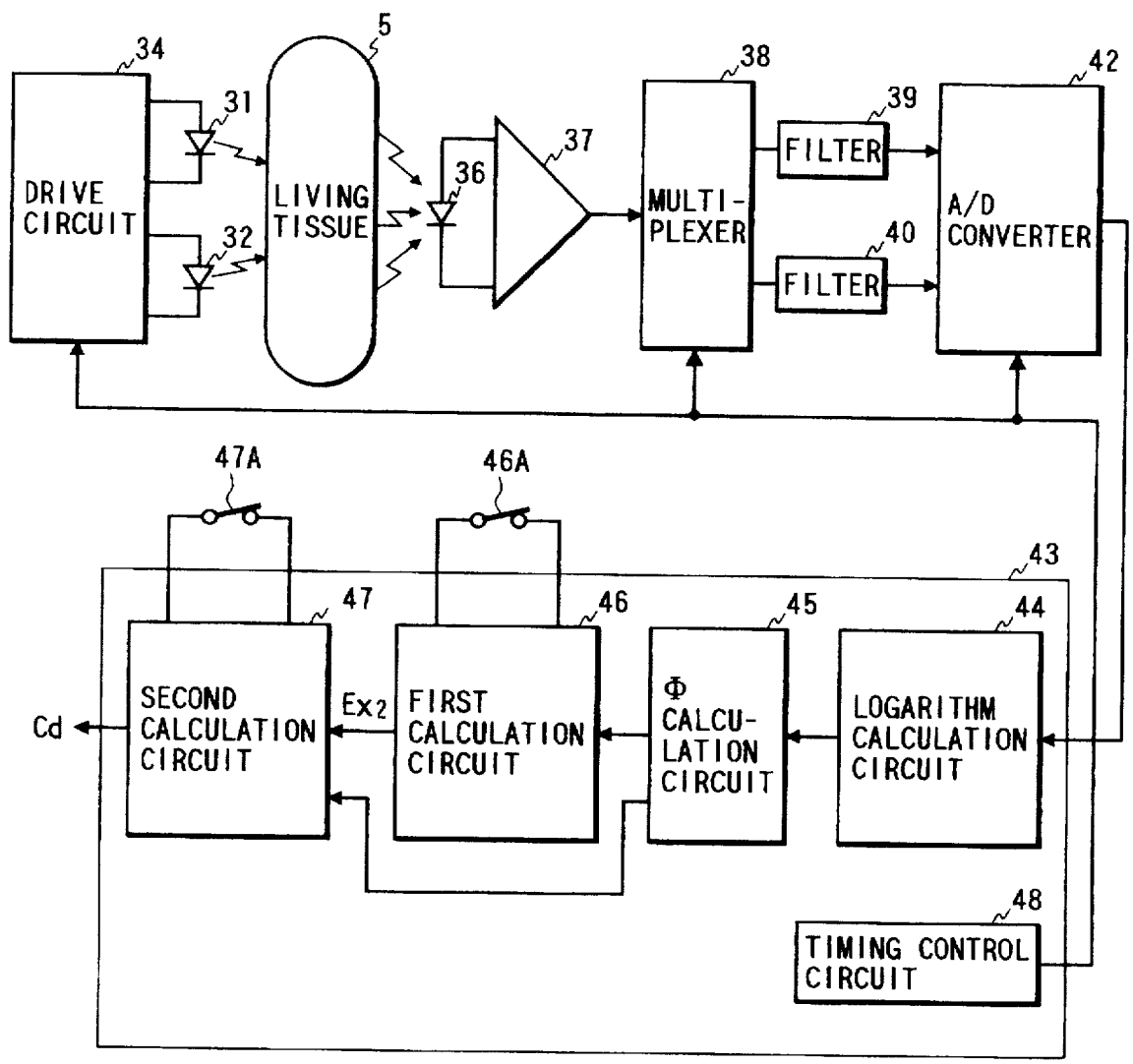
FIG. 10 is a block diagram showing an overall arrangement of a fifth embodiment of the present invention.

The dye dilution curve measuring apparatus based on the above-mentioned principles will be described. FIG. 10 shows in block diagram an overall arrangement of the dye dilution curve measuring apparatus.

Light emitting elements 31 and 32, when driven by a drive circuit 34, emit light beams of the wavelengths $\lambda 1$ and $\lambda 2$. These light beams are transmitted through a living tissue 5, and the, light beams emanating from the tissue are converted into corresponding electrical signals. These signals are amplified by an amplifier 7, and then a multiplexer 38 directs these amplified signals to the filters 39 and 40 in accordance with the wavelengths of the light beams. The filters 39 and 40 filter out unnecessary high frequency components of the electrical signals, an A/D converter 42 converts the electrical signals from the filters into digital signals, and the digital signals are inputted to a data processor 43. The data processor 43 is made up of a logarithm calculation circuit 44, a $\Phi$ calculation circuit 45, a first calculation circuit 46, a second calculation circuit 47, and a timing control circuit 48. The timing control circuit 48 sends timing signals to the drive circuit 34, multiplexed 38, A/D converter 42, and the data processor 43, thereby time controlling the operations of these functional components. The first calculation circuit 46 is provided with a switch 46A for indicating its operation start, and the second calculation circuit 47 is provided with a switch 47A for indicating dye injection.

The logarithm calculation circuit 44 receives I1 and I2 as the output signals of the A/D converter 42, and calculates the logarithmic values lnI1 and lnI2 thereof.

The $\Phi$ calculation circuit 45 extracts pulsative components from the logarithmic signals lnI1 and lnI2 outputted from the logarithm calculation circuit 44, and calculates $\Phi_{12} = \ln I1 / \Delta \ln I2$.

Before dye injection, when an operator turns on the switch 46A, the first calculation circuit 46 puts the value of $\Phi_{12}$, derived from the $\Phi$ calculation circuit 45, into the equation (35), and calculates Ex2.

When dye is injected and the operator turns on the switch 47A, the second calculation circuit 47 uses Ex2, which is derived from the first calculation circuit 46, and $\Phi_{12}$, which is outputted from the $\Phi$ calculation circuit 45, in the equation (36), thereby calculating the equation (36). When the second calculation circuit 47 successively repeats this process, a dye dilution curve is obtained.

Sixth Embodiment

Figure 11:
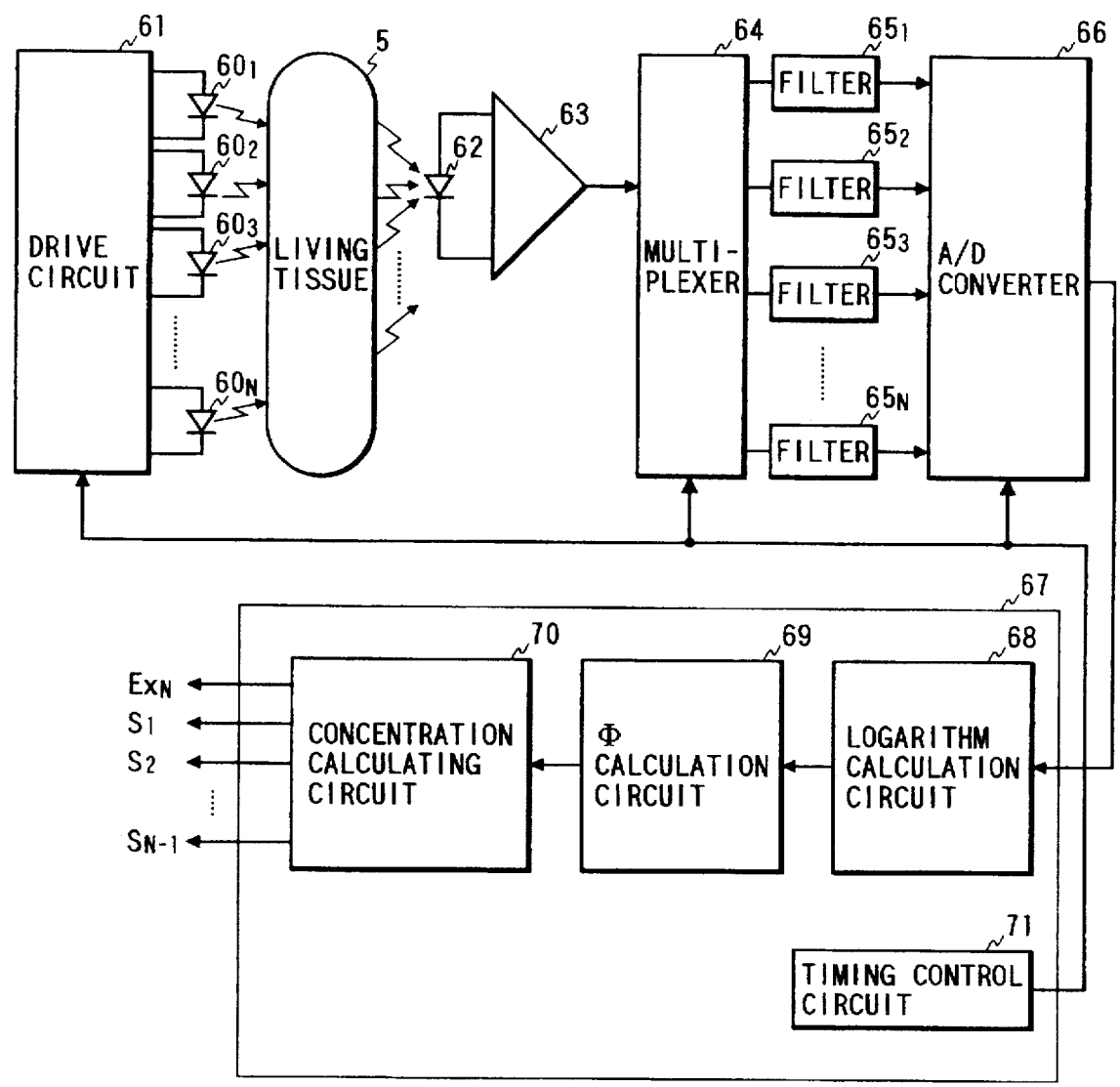
FIG. 11 is a block diagram showing an overall arrangement of a sixth embodiment of the present invention.

A sixth embodiment of the present invention will be described. An apparatus according to the sixth embodiment of the present invention is an apparatus for determining the concentration of (N−1) kinds of light absorbing materials, which include not only oxyhemoglobin and reduction hemoglobin but also other hemoglobin or light absorbing materials. FIG. 11 shows in block diagram an overall arrangement of the apparatus.

Light emitting elements $60_1, 60_2, \ldots, 60_N$, when driven by a drive circuit 61, emit light beams of the wavelengths $\lambda 1, \lambda 2, \ldots, \lambda N$. These light beams are transmitted through a living tissue 5, and received and converted into corresponding electrical signals by a photo sensing element 62. These signals are amplified by an amplifier 63, and then a multiplexer 64 directs these amplified signals to the filters $65_1, 65_2, \ldots, 65_N$ in accordance with the wavelengths of the light beams. The filters $65_1, 65_2, \ldots, 65_N$ filter out unnecessary high frequency components of the electrical signals, an A/D converter 66 converts the electrical signals from the filters into digital signals, and the digital signals are inputted to a data processor 67. The data processor 67 is made up of a logarithm calculation circuit 68, a $\Phi$ calculation circuit 69, a concentration calculating circuit 70, and a timing control circuit 71. The timing control circuit 71 sends timing signals to the drive circuit 61, multiplexed 64, A/D converter 66, and the data processor 67, thereby time controlling the operations of these functional components.

The logarithm calculation circuit 68 logarithmically calculates the output signals I1, I2, ..., IN of the A/D converter 66 into logarithmic signals lnI1, lnI2, ..., lnIN.

The $\Phi$ calculation circuit 69 extracts pulsative components from the logarithmic signals lnI1, lnI2, ... lnIN outputted from the logarithm calculation circuit 68, and calculates $\Phi_{12}=\Delta \ln I1/\Delta \ln I2$ and $\Phi_{32}=\Delta \ln I3/\Delta \ln I2$, ..., $\Phi_{N2}=\Delta \ln IN/\Delta \ln I2$.

The concentration calculating circuit 70 calculates the following equation:

$$\Phi_{12} = [\{(E(1)_1S(1) + E(2)_1S(2) + \ldots + E(N-1)_1S(N-1)) \quad (38)$$
$$(E(1)_1S(1) + E(2)_1S(2) + \ldots + E(N-1)_1S(N-1) + F)\}^{1/2} - Ex_1]/$$
$$[\{(E(1)_2S(1) + E(2)_2S(2) + \ldots + E(N-1)_2S(N-1)(E(1)_2S(1) +$$
$$E(2)_2S(2) + \ldots + E(N-1)_2S(N-1) + F)\}^{1/2} - Ex_2]$$
$$(i = 1,3,4,5 \ldots ,N)$$

E(j) (j=1, 2, ..., N−1): extinction coefficients of various kinds of hemoglobin or one of other light absorbing materials S(J) (j=1, 2, ..., N−1): concentration ratio of a hemoglobin or one of other light absorbing materials to all of various kinds of hemoglobin Ex1, Ex2, ..., ExN: tissue terms at the wavelengths $\lambda 1, \lambda 2, \ldots, \lambda N$.

As described in the first embodiment, the following mutual relation is present among Ex1, Ex2, ..., ExN.

$$Exi = aiEx2 + bi (i=1, 3, 4, \ldots, N) \quad (39)$$

The concentration calculating circuit 70 puts $\Phi_{12}, \Phi_{32}, \ldots, \Phi_{N2}$, which are outputted from the $\Phi$ calculation circuit 69, into the equation led from these equations, and calculates Ex2, S(1), S(2), ..., S(N).

a) Specific example 1 of the sixth embodiment

Where three kinds of hemoglobin, $O_2Hb$, RHb, and COHb are contained in blood, the unknowns are the following three:

Ex2: tissue term of the wavelength $\lambda_2$

So: concentration ratio of $O_2Hb$ to all of the hemoglobin

Sc: concentration ratio of $_{CO}Hb$ to all of the hemoglobin

The concentration Sr of RHb to all of the hemoglobin, if So and Sc are known, is given by Sr=1−(So+Sc). In this case, the measurement is possible by using four wavelengths of light. The concentration calculating circuit 70 calculates the equations (38) and (39) when N=4, to thereby obtain Ex2, So, and Sc. The equation (38) is rewritten into $$\Phi_{12} = \quad (40)$$
$$[\{(Eo_1So + Er_1Sr + Ec_1Sc)(Eo_1So + Er_1Sr + Ec_1Sc + F)\}^{1/2} - Ex_1]/$$
$$[\{(Eo_2So + Er_2Sr + Ec_2Sc)(Eo_2So + Er_2Sr + Ec_2Sc + F)\}^{1/2} - Ex_2]$$

$$\Phi_{32} = \quad (41)$$
$$[\{(Eo_3So + Er_3Sr + Ec_3Sc)(Eo_3So + Er_3Sr + Ec_3Sc + F)\}^{1/2} - Ex_3]/$$
$$[\{(Eo_2So + Er_2Sr + Ec_2Sc)(Eo_2So + Er_2Sr + Ec_2Sc + F)\}^{1/2} - Ex_2]$$

$$\Phi_{42} = \quad (42)$$
$$[\{(Eo_4So + Er_4Sr + Ec_4Sc)(Eo_4So + Er_4Sr + Ec_4Sc + F)\}^{1/2} - Ex_4]/$$
$$[\{(Eo_2So + Er_2Sr + Ec_2Sc)(Eo_2So + Er_2Sr + Ec_2Sc + F)\}^{1/2} - Ex_2]$$

Eo: extinction coefficient of $O_2Hb$
Er: extinction coefficient of RHb
Ec: extinction coefficient of COHb b) Specific example 2 of the sixth embodiment Where two kinds of hemoglobin $O_2Hb$ and RHb are contained in blood and another light absorbing material, bilirubin, is also contained, the unknowns are Ex2: tissue term of the wavelength So: concentration ratio of $O_2Hb$ to all of the hemoglobin Cp/Hb: concentration ratio of bilirubin to hemoglobin The concentration Sr of RHb to the total hemoglobin, if So is known, is given by Sr=1−(So+Sc). Also in this case, the measurement is possible by using four wavelengths of light. It is assumed that light of the wavelength $\lambda_2$ is not absorbed by bilirubin. The concentration calculating circuit 70 calculates the equations (38) and (39) when N=4, to thereby obtain nEx2, So, and Cp/Hb. The equation (38) is rewritten into:

$$\Phi_{12} = [\{(Eo_1So + Er_1Sr + Ep_1Cp/Hb) \quad (43)$$
$$(Eo_1So + Er_1Sr + Ep^1Cp/Hb + F)\}^{1/2} - Ex_2]/$$
$$[\{(Eo_2So + Er_2Sr)(Eo_2So + Er_2Sr + F)\}^{1/2} - Ex_2]$$

$$\Phi_{32} = [\{(Eo_3So + Er_3Sr + Ep_3Cp/Hb) \quad (44)$$
$$(Eo_3So + Er_3Sr + Ep_3Cp/Hb + F)\}^{1/2} - Ex_3]/$$
$$[\{(Eo_2So + Er_2Sr)(Eo_2So + Er_2Sr + F)\}^{1/2} - Ex_2]$$

$$\Phi_{42} = [\{(Eo_4So + Er_4Sr + Ep_4Cp/Hb) \quad (45)$$
$$(Eo_4So + Er_4Sr + Ep_4Cp/Hb + F)\}^{1/2} - Ex_3]/$$

-continued $$[\{(Eo_2So + Er_2Sr)(Eo_2So + Er_2Sr + F)\}^{1/2} - Ex_2]$$

where Ep: extinction coefficient of bilirubin.

c) Specific example 3 of the sixth embodiment

Where two kinds of hemoglobin, $O_2Hb$ and RHb are contained in blood, and another dye is injected into blood, the unknowns are:

Ex2: tissue term of the wavelength $\lambda_2$

So: concentration ratio of $O_2Hb$ to all of the hemoglobin

Cd/Hb: concentration ratio of injected dye to hemoglobin

The concentration Sr of RHb to the total hemoglobin is obtained if So is known. Also in this case, by using four wavelengths of light, when another dye is injected into blood, the dye concentration can be calculated without storing the value of Ex2 before dye injection, as in the case where dye has been present in blood. It is assumed that light of the wavelength $\lambda_2$ is not absorbed by the dye. The concentration calculating circuit 70 calculates the equations (38) and (39) when N=4, to thereby obtain Ex2, So, and Cp/Hb. The equation (38) is rewritten into $$\Phi_{12}=[\{(Eo_1So+Er_1Sr+Ed_1Cd/Hb)(Eo_1So+Er_1Sr+Ed_1Cd/Hb+F)\}^{1/2}-Ex_1]/[\{(Eo_2So+Er_2Sr)(Eo_2So+Er_2Sr+F)\}^{1/2}-Ex_2] \quad (46)$$

$$\Phi_{32}=[\{(Eo_3So+Er_3Sr+Ed_3Cd/Hb)(Eo_3So+Er_3Sr+Ed_3Cd/Hb+F)\}^{1/2}-Ex_3]/[\{(Eo_2So+Er_2Sr)(Eo_2So+Er_2Sr+F)\}^{1/2}-Ex_2] \quad (47)$$

$$\Phi_{42}=[\{(Eo_4So+Er_4Sr+Ed_4Cd/Hb)(Eo_4So+Er_4Sr+Ed_4Cd/Hb+F)\}^{1/2}-Ex_4]/[\{(Eo_2So+Er_2Sr)(Eo_2So+Er_2Sr+F)\}^{1/2}-Ex_2] \quad (48)$$

where Ed: extinction coefficient of dye in blood.

Seventh Embodiment

Figure 12:
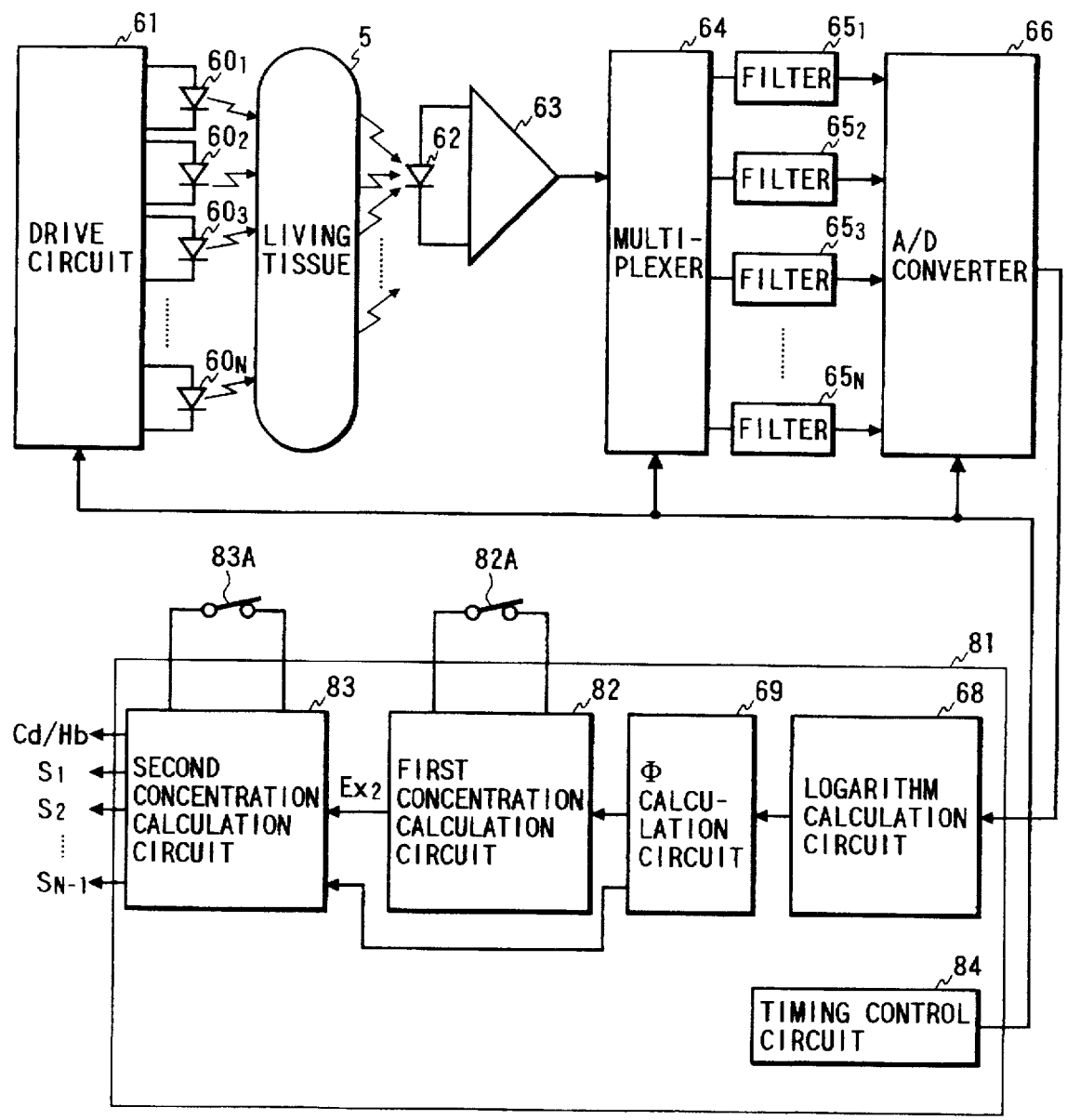
FIG. 12 is a block diagram showing an overall arrangement of a seventh embodiment of the present invention.

A seventh embodiment of the present invention will be described. An apparatus according to the seventh embodiment of the present invention is a dye dilution curve measuring apparatus. In a case where (N−1) kinds of light absorbing materials, which include not only oxyhemoglobin and reduced hemoglobin but also other hemoglobin or light absorbing materials, are contained in blood, dye is injected into blood and the concentration of injected dye is determined by the apparatus of the present invention. FIG. 12 shows in block diagram an overall arrangement of the apparatus.

As in the apparatus of FIG. 12, light emitting elements $60_1, 60_2, \ldots, 60_N$, when driven by a drive circuit 61, emit light beams of the wavelengths $\lambda 1, \lambda 2, \ldots, \lambda N$. These light beams are transmitted through a living tissue 5 and received and converted into corresponding electrical signals by a photo sensing element 62. These signals are amplified by an amplifier 63, and then a multiplexed 64 directs these amplified signals to the filters $65_1, 65_2, \ldots, 65_N$ in accordance with the wavelengths of the light beams. The filters $65_1, 65_2, \ldots, 65_N$ filter out unnecessary high frequency components of the electrical signals, an A/D converter 66 converts the electrical signals from the filters into digital signals, and the digital signals are inputted to a data processor 81. The data processor 81 is made up of a logarithm calculation circuit 68, a $\Phi$ calculation circuit 69, a first concentration calculating circuit 82, a second concentration calculating circuit 83, and a timing control circuit 84. The timing control circuit 84 sends timing signals to the drive circuit 61, multiplexer 64, A/D converter 66, and the data processor 81, thereby time controlling the operations of these functional components. The first concentration calculating circuit 82 is provided with an operation start switch 82A. The second concentration calculating circuit 93 is provided with a switch 83A for indicating an operation start and a dye injection.

The logarithm calculation circuit 68 logarithmically calculates the output signals I1, I2, . . . , IN of the A/D converter 66 into logarithmic signals lnI1, lnI2, . . . , lnIN.

The $\Phi$ calculation circuit 69 extracts pulsative components from the logarithmic signals lnI1, lnI2, . . . lnIN outputted from the logarithm calculation circuit 68, and calculates $\Phi_{12}=\Delta lnI1/\Delta lnI2$ and $\Phi_{32}=\Delta lnI3/\Delta lnI2$, . . . , $\Phi_{N2}=\Delta lnIN/\Delta lnI2$.

Before dye injection, when an operator turns on the switch 82A, the first concentration calculating circuit 82 performs, on the basis of $\Phi_{12}, \Phi_{32}, \ldots, \Phi_{N2}$, the calculations to obtain the tissue term Ex2 on the wavelength $\lambda_N$ and a concentration ratio S(j) (j=1, 2, . . . , N−1) of hemoglobin or other light absorbing materials to the total of hemoglobin. The calculations are the same as those performed by the concentration calculating circuit 70 in the sixth embodiment, and hence no further description thereof will be given here. In this way, Ex2 is obtained. This value Ex2 is assumed to be constant after dye is injected also.

When dye is injected and the switch 83A is turned on, the second concentration calculating circuit 83 performs calculations using Ex2, which is received from the first concentration calculating circuit 82, $\Phi_{12}, \Phi_{32}, \ldots, \Phi_{N2}$, which are received from the $\Phi$ calculation circuit 69, the following equations, to thereby obtain Cd/Hb (dye concentration/hemoglobin concentration) and S(j) (j=1, 2, . . . , N−1).

$$\Phi_{12} = [\{(E(1)_1S(1) + E(2)_1S(2) + \ldots + E(N-1)_1S(N-1) + \quad (49)$$

$$Ed_1Cd/Hb)(E(1)_1S(1) + E(2)_1S(2) + \ldots + E(N-1)_1S(N-1) +$$

$$Ed_1Cd/Hb + F)\}^{1/2} - Ex_1]/[\{(E(1)_2S(1) + E(2)_2S(2) + \ldots +$$

$$E(N-1)_2S(N-1) + Ed_2Cd/Hb)(E(1)_2S(1) + E(2)_2S(2) +$$

$$\ldots E(N-1)_2S(N-1) + Ed_2Cd/HbF)\}^{1/2} - Ex_2](i = 1, 3, 4, \ldots, N)$$

$$Exi = aiEx2 + bi(i = 1, 3, 4, \ldots, N) \quad (50)$$

E(j) (J=1, 2, . . . , N−1): extinction coefficients of various kinds of hemoglobin or other light absorbing materials S(j) (j=1, 2, . . . , N−1): concentration ratio of a hemoglobin or other light absorbing materials to all of the total hemoglobin Ex1, Ex2, . . . , EN: tissue terms at the wavelengths $\lambda 1$, $\lambda 2, \ldots, \lambda N$.

a) Specific example 1 of the seventh embodiment

Where three kinds of hemoglobin, $O_2Hb$, RHb, and COHb are contained in blood before dye injection, the unknowns are the following three:

Ex2: tissue term of the wavelength $\lambda_2$

So: concentration ratio of $O_2Hb$ to the total hemoglobin

Sc: concentration ratio of $_{CO}Hb$ to all of the total hemoglobin

The concentration Sr of RHb to the total hemoglobin, if So and Sc are known, can be obtained. In this case, the measurement is possible by using four wavelengths of light as in the specific example 1 in the sixth embodiment. The first concentration calculating circuit 82 performs the calculations for Ex2, So, and Sc before dye injection. When dye is injected, the second concentration calculating circuit 83 performs the calculations of the equations (49) and (50) when N=4 while using Ex2 outputted from the first concentration calculating circuit 82, thereby obtaining So, Sc, and Cd/Hb. In this case, the equation (49) is rewritten into:

$$\Phi_{12} = [\{(Eo_1So + Er_1Sr + Ec_1Sc + Ed_1Cd/Hb)(Eo_1So + Er_1Sr + \quad (51)$$
$$Ec_1Sc + Ed_1Cd/Hb + F)\}^{1/2} - Ex_1]/[\{(Eo_2So + Er_2Sr +$$
$$Ec_2Sc)(Eo_2So + Er_2Sr + Ec_2Sc + F)\}^{1/2} - Ex_2]$$

$$\Phi_{32} = [\{(Eo_3So + Er_3Sr + Ec_3Sc + Ed_3Cd/Hb)(Eo_3So + \quad (52)$$
$$Er_3Sr + Ec_3Sc + Ed_3Cd/Hb + F)\}^{1/2} - Ex_3]/[\{(Eo_2So +$$
$$Er_2Sr + Ec_2Sc)(Eo_2So + Er_2Sr + Ec_2Sc + F)\}^{1/2} - Ex_2]$$

$$\Phi_{42} = [\{(Eo_4So + Er_4Sr + Ec_4Sc + Ed_4Cd/Hb)(Eo_4So + \quad (53)$$
$$Er_4Sr + Ec_4Sc + Ed_4Cd/Hb + F)\}^{1/2} - Ex_4]/[\{(Eo_2So +$$
$$Er_2Sr + Ec_2Sc)(Eo_2So + Er_2Sr + Ec_2Sc + F)\}^{1/2} - Ex_2]$$

where $8o_2$: wavelength of light not absorbed by injected dye.

b) Specific example 2 of the seventh embodiment

Where two kinds of hemoglobin, $O_2Hb$ and RHb, and bilirubin, are contained in blood before dye injection, the unknowns are the following three;

Ex2: tissue term of the wavelength $\lambda_2$

So: concentration ratio of $O_2Hb$ to the total hemoglobin

Cp/Hb: bilirubin concentration/hemoglobin concentration

The concentration Sr of RHb to all of the hemoglobin, if So is known, can be obtained. In this case, the measurement is possible by using four wavelengths of light as described in the specific example 2. The first concentration calculating circuit 82 performs the calculations for Ex2, So, and Cp/Hb before dye injection. When dye is injected, the second concentration calculating circuit 83 performs the calculations of the equations (49) and (50) when N=4 while using Ex2 outputted from the first concentration calculating circuit 82, thereby obtaining So, Sc and Cd/Hb. In this case, the equation (49) is rewritten into:

$$\Phi_{12} = [\{(Eo_1So + Er_1Sr + Ep_1Cp/Hb + Ed_1Cd/Hb)(Eo_1So + \quad (54)$$
$$Er_1Sr + Ep_1Cp/Hb + Ed_1Cd/Hb + F)\}^{1/2} - Ex_1]/[\{(Eo_2So +$$
$$Er_2Sr + Ep_2Cp/Hb)(Eo_2So + Er_2Sr + Ep_2Cp/Hb + F)\}^{1/2} - Ex_2]$$

$$\Phi_{32} = [\{(Eo_3So + Er_3Sr + Ep_3Cp/Hb + Ed_3Cd/Hb)(Eo_3So + \quad (55)$$
$$Er_3Sr + Ep_3Cp/Hb + Ed_3Cd/Hb + F)\}^{1/2} - Ex_3]/[\{(Eo^2So +$$
$$Er_2Sr + Ep_2Cp/Hb)(Eo_2So + Er_2Sr + Ep_2Cp/Hb + F)\}^{1/2} - Ex_2]$$

$$\Phi_{42} = [\{(Eo_4So + Er_4Sr + Ep_4Cp/Hb + Ed_4Cd/Hb)(Eo_4So + \quad (56)$$
$$Er_4Sr + Ep_4Cp/Hb + Ed_4Cd/Hb + F)\}^{1/2} - Ex_4]/[\{(Eo_2So +$$
$$Er_2Sr + Ep_2Cp/Hb)(Eo_2So + Er_2Sr + Ep_2Cp/Hb + F)\}^{1/2} - Ex_2]$$

where $\lambda_2$: wavelength of light not absorbed by injected dye.

In the above-mentioned embodiments, the data processor is made up of separate circuits. However, a computer may be used for the data processor. In this case, the processes carried out by a CPU correspond to these separate circuits.

In the above-mentioned embodiments, if $\Delta$lnI indicates the amplitude of lnI, it can be approximated to the ratio of an AC component of I to DC component thereof. $\Delta$lnI1/$\Delta$lnI2, which represents the logarithmic amplitude, may be substituted by any of the following ratios and inclination. The same thing is true for $\Delta$lnI3/$\Delta$lnI2.

1) Ratio of varying quantities of lnI1 and lnI2 for a fixed time interval.

2) Ratio of inclinations of the regression lines of lnI1 and lnI2 with respect to time for a fixed time interval.

3) Inclinations of the regression lines lnI1 and lnI2 for a fixed time interval.

What is claimed is:

1. An apparatus for determining a concentration of at least one of a tissue term and light absorbing materials in blood comprising:

light generating means for generating light beams of different wavelengths;

photoelectric transducing means for converting light beams, which are emitted from the light generating means, and transmitted through a tissue of living body, into electrical signals;

pulsation calculating means for calculating pulsations of absorbency of the tissue of living body for each wavelength on the basis of output signals from the photoelectric transducing means;

pulsation ratio calculating means for calculating a ratio of the pulsations of the absorbency of each wavelength, calculated by the pulsation calculating means; and first concentration calculating means for performing the calculations of a value of said tissue term on the basis of an output signal from the pulsation ratio calculating means using a formula having a single unknown on the tissue term, which is constructed on the basis of the fact that a predetermined relation is present between the tissue terms of the different wavelengths.

2. The apparatus according to claim 1, wherein the predetermined relation, which is present between the tissue terms of the different wavelengths, is such a relation that each tissue term is expressed by a linear function of a single tissue term.

3. The apparatus according to claim 1, further comprising:

indicating signal generating means for generating an indication signal after dye has been injected into the blood;

second concentration calculating means for performing the calculations of at least one of a concentration value of dye in blood and the concentration of light absorbing materials in blood on the basis of the output signal from the pulsation ratio calculating means after the indicating signal generating means generates an indication signal, using the value of a tissue term obtained by the first concentration calculating means.

4. The apparatus according to claim 3, wherein the concentration value of dye in the first calculating means is set to zero.

5. The apparatus according to claim 1, wherein said first concentration calculating means further performs the calculation of the concentration of light absorbing material in blood on the basis of said output signal from said pulsation ratio calculating means using said formula.

6. A method for determining at least one of a tissue term and a concentration of light absorbing materials, comprising the steps of:

generating light beams of different wavelengths;

converting light beams, which are emitted from light generating means, and transmitted through a tissue of living body, into electrical signals;

calculating a pulsation of an absorbance of the tissue of a living body for each wavelength on the basis of output signals from a photoelectric transducing means;

calculating a ratio of the pulsations of the absorbency of each wavelength, which are calculated by pulsation calculating means; and performing the calculations of a value of said tissue term on the basis of an output signal from the pulsation ratio calculating means, and calculating a formula having a single unknown on the tissue term, which is constructed on the basis of the fact that a predetermined relation is present between the tissue terms of the different wavelengths.

7. The method according to claim 6, further comprising the step of:

performing the calculations of the concentration of light absorbing materials in blood on said calculated value of a tissue term and said calculated ratio of the pulsations of the absorbence of each wavelength.

8. The method according to claim 6, further comprising the steps of:

performing the calculation of the concentration of light absorbing materials in blood on said value of said tissue term and said ratio of the pulsations of the absorbence of each wavelength.

9. An apparatus for determining at least one of a value of a tissue term and a concentration of light absorbing materials, comprising:

light generating means for generating light beams of different wavelengths;

photoelectric transducing means for converting light beams, which are emitted from the said light generating means, and transmitted through a tissue of living body into electrical signals;

pulsation calculating means for calculating pulsations of absorbency of the tissue of the living body for each wavelength on the basis of output signals of said photoelectric transducing means;

pulsation ratio calculating means for calculating ratios of the pulsations of the absorbency of each wavelength calculated by said pulsation calculating means; and first concentration calculating means for performing the calculations of said value of said tissue term and the concentration of light absorbing materials on the basis of an output signal from the pulsation ratio calculating means using a formula having a single unknown on the tissue term, which is constructed on the basis of the fact that a predetermined relation is present between the tissue terms of the different wavelengths.

10. The apparatus according to claim 9, wherein the predetermined relation which is present between the tissue terms of the different wavelengths is such a relation that each tissue term is expressed by a linear function of a single tissue term.

11. The apparatus according to claim 9, further comprising:

indicating signal generating means for generating an indication signal after dye has been injected into the blood;

second concentration calculating means for performing the calculation of at least one of a concentration value of dye in blood and the concentration of light absorbing materials in blood on the basis of an output signal from said pulsation ratio calculating means after said indication signal generating means generates said indication signal, using the value of a tissue term obtained by said first concentration calculating means.

12. The apparatus according to claim 9, wherein the concentration value of dye in the first calculating means is set to zero.

13. A method for determining at least one of a value of a tissue term and a concentration of light absorbing materials, comprising the steps of:

generating light beams of different wavelengths;

converting light beams, which are emitted from light generating means, and transmitted through a tissue of living body, into electrical signals;

calculating a pulsation ratio of an absorbance of the tissue of the living body for each wavelength on the basis of output signals from a photoelectric transducing means;

calculating ratios of the pulsations of the absorbency of each wavelength which are calculated by pulsation calculating means; and performing the calculations of said value of said tissue term and the concentration of light absorbing materials on the basis of an output signal from the pulsation ratio calculating means, and calculating a formula having a single unknown on the tissue term, which is constructed on the basis of the fact that a predetermined relation is present between the tissue term of the different wavelengths.

* * * * *